United States Patent [19]

McAuslan

[11] Patent Number: 4,592,084
[45] Date of Patent: May 27, 1986

[54] DENTAL X-RAY HOLDER FOR USE IN ENDODONTICS

[76] Inventor: David N. McAuslan, 1502 Avalon Ct., St. Charles, Ill. 60174

[21] Appl. No.: 570,084
[22] Filed: Jan. 12, 1984
[51] Int. Cl.⁴ .............................................. G03B 42/02
[52] U.S. Cl. ..................................... 378/170; 378/168
[58] Field of Search ........................ 378/168, 169, 170

[56] References Cited

U.S. PATENT DOCUMENTS 4,489,427 12/1984 Allison ................................ 378/168
4,507,798 3/1985 Welander ............................ 378/168

Primary Examiner—Craig E. Church
Attorney, Agent, or Firm—Gary, Jeuttner & Pyle

[57] ABSTRACT

A dental X-ray holder for use in endodontics, for positioning a dental X-ray film in a predetermined position in the mouth for retention of the film in a given position at each placement of the holder by the patient's bite on the holder, comprises a film retaining member having an inner tongue and an outer tongue defining a slot therebetween for receiving and holding an X-ray film packet; two spaced apart side walls integral with the respective side edges of the film retaining member, the side walls together with the film retaining member defining a U-shaped area therebetween for accommodating endodontic equipment, such as a rubber dam clamp and root canal files; two flanges, the transverse edge of each flange integral with the upper edge of the adjacent side wall and the longitudinal edge of each flange integral with the adjacent portions of the upper edge of the film retaining member for providing rigidity; and a positioning arm which may be removably attached to either side wall.

6 Claims, 5 Drawing Figures

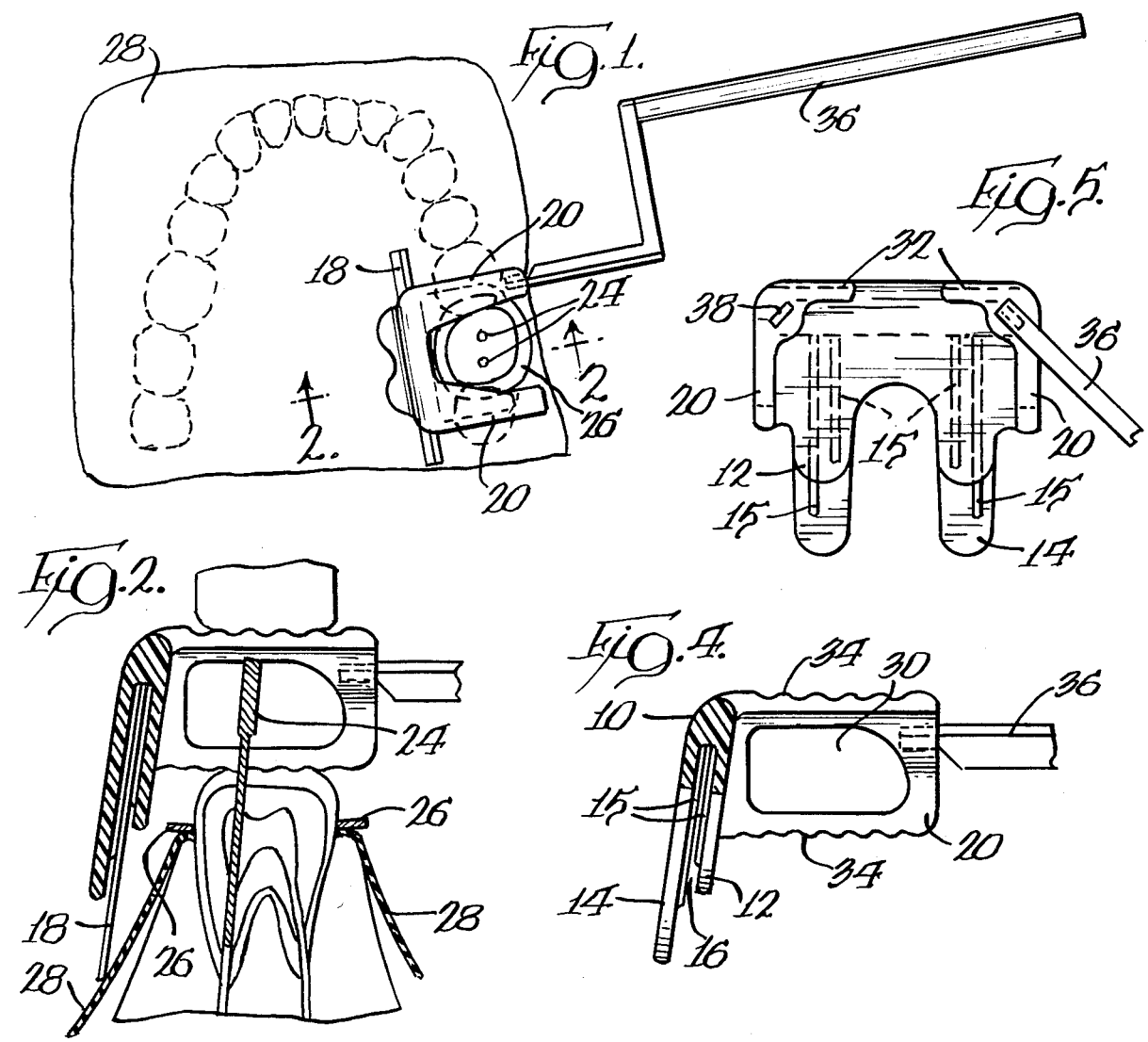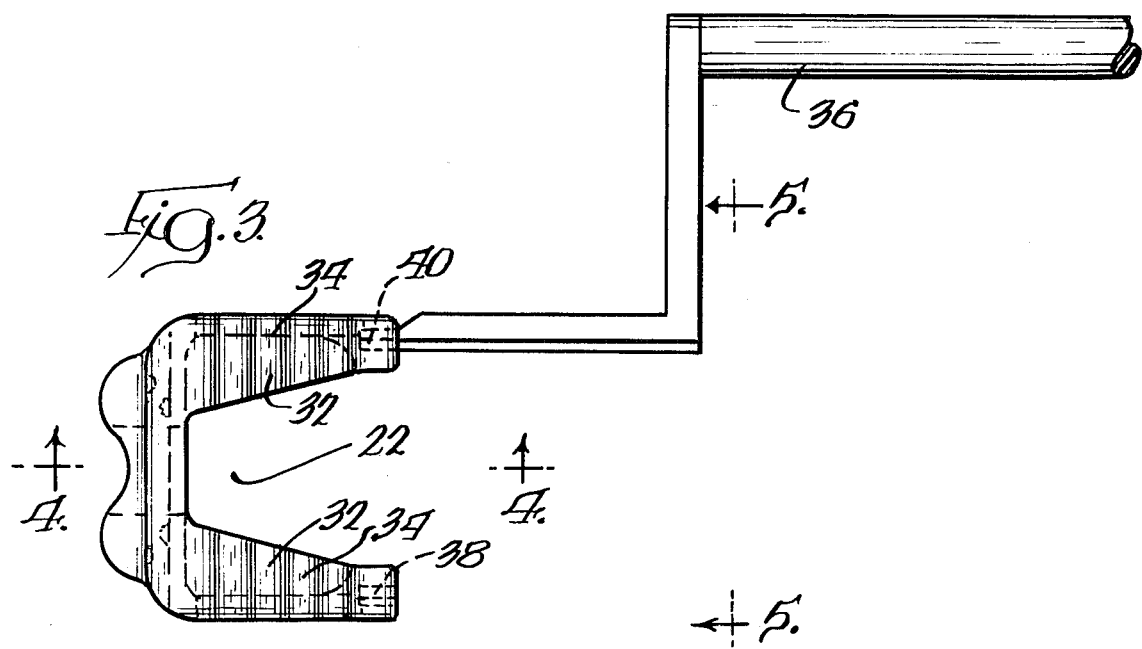

DENTAL X-RAY HOLDER FOR USE IN ENDODONTICS

BACKGROUND OF THE INVENTION

This invention relates to dental X-ray film holders for positioning dental X-ray film in a predetermined position in the mouth and for retention of the film in a given position at each placement of the holder by the patient's bite on the holder, for use in taking normal diagnostic radiographs, and specially for taking "wire measure" radiographs.

The prior art shows a number of dental X-ray holders for use in general dentistry, such as those shown in U.S. Pat. Nos. 2,876,947 to Lieberman, 2,899,559 to Maurer, and 3,304,422 and 3,304,423 both to Medwedeff. Unfortunately, none of the prior art holders are suitable for use in endodontics.

In performing root canal therapy, the dentist or endodontist will remove the pulp tissue (nerves) from the tooth. This is accomplished by drilling holes downwardly through the tooth and removing the pulp tissue (nerve) with steel files or barbed broaches. In performing this task, it is often necessary for the dentist or endodontist to determine how deep into the canal he or she is working in relation to the end of the tooth and the patient's jaw bone. This is typically accomplished by a procedure known as "wire measure" radiographs, whereby the endodontist inserts steel root canal file(s) into the canals of the tooth and then takes a radiograph (X-ray) of the tooth. In addition to the file(s) protruding from the patient's tooth, the dentist or endodontist will have several other pieces of equipment in the patient's mouth, namely a rubber dam (which is a thin latex membrane which covers the patient's mouth save for the tooth being worked on, to minimize exposure of the subject tooth to bacteria) and a rubber dam clamp (which is a steel clamp that retains the rubber dam to the subject tooth). The prior art X-rayholders are not suitable for use in taking wire measure radiographs, inasmuch as they manifestly interfere with the rubber dam clamp and the files. As a result, the X-ray film is typically held in place by the patient with his finger, which is most cumbersome and often results in slippage of the film, and thereby wasted time and radiographs.

It would be desirable to have a dental X-ray holder for use in general dentistry and endodontics which will securely hold the X-ray film in place and accommodate, without interference, endodontic and other similar equipment.

OBJECT OF THE INVENTION

The object of the invention is to provide a dental X-ray holder which may be securely held in place by the patient between his upper and lower teeth, by biting down thereon; which may be used in taking normal diagnostic radiographs; which may be used in taking wire measure radiographs; which may accommodate anterior and posterior types of X-ray film; and which may be used in connection with X-raying upper and lower teeth, right and left side, incisors, canines, bicuspids and molars.

SUMMARY OF THE INVENTION

In accordance with the present invention, a dental X-ray holder is provided for positioning dental X-ray film in a predetermined position in the mouth and for retaining the film in a given position at each placement of the holder by the patient's bite on the holder. The holder comprises a film retaining member for receiving and holding an X-ray film packet and two spaced apart side walls integral with respective side edges of the film retaining member. The film retaining member has an outer tongue and an inner tongue defining a slot therebetween for receiving and holding a X-ray film packet. The inner tongue and outer tongue have nubs thereon for securely retaining the film packet. The side walls and the film retaining member together define a U-shaped area therebetween for accommodation, without obstruction, of the rubber dam clamp and root canal files, thus overcoming the primary disadvantages of the prior art holders. In the preferred embodiment, the side walls have windows therein for providing maximum viewing of the endodontic root canal files.

Also in the preferred embodiment, the holder further comprises two flanges integral on their respective transverse edges with the upper edge of the adjacent side walls, respectively, and on their longitudinal edges with the upper edge of the adjacent portions of film retaining member, for providing additional rigidity and durability. The top surface of the flanges and the bottom surface of the side walls may be provided with gripping ridges to insure that the holder does not slip after it has been positioned.

Finally, the holder may be provided with either an integral or removable positioning arm, to assist in positioning the holder in the patient's mouth. The positioning arm may also be used for aiming the X-ray gun.

Thus, the unique configuration of the holder of the invention overcomes the attendant problems in the prior art. The U-shaped area between the side walls accommodates, without interference, the rubber dam clamp and root canal files. Maximum viewing of the subject tooth and root canal files is provided by the windows in the side walls. The holder may be used in endodontics and may additionally be used for taking normal radiographs in general dentistry. The slotted film retaining member can accommodate both anterior and posterior types of X-ray film. Finally, the holder may be used in any area of the mouth, anterior or posterior, right or left, upper or lower.

Further objects and advantages of the invention will become apparent from the following detailed description, as read in conjunction with the accompanying drawings.

BRIEF DESCRIPTION OF THE DRAWINGS

FIG. 1 is a plan view of the patient's lower jaw illustrating the preferred embodiment of the film holder of the invention overlying the patient's right first molar.

FIG. 2 is a cross sectional view taken substantially along line 2—2 of FIG. 1.

FIG. 3 is a top plan view of the preferred embodiment of the film holder.

FIG. 4 is a transverse cross section of the preferred embodiment of the film holder taken along line 4—4 of FIG. 3.

FIG. 5 is a front elevation of the preferred embodiment of the film holder, the view being taken substantially along line 5—5 of FIG. 3.

DETAILED DESCRIPTION

Referring to the drawings, the preferred embodiment of the film holder of the invention comprises a film retaining member 10 having an inner tongue 12 and an outer tongue 14 defining a slot 16 therebetween for receiving a X-ray film packet 18; and two spaced apart side walls 20 integral with the respective side edges of the film retaining member 10; the side walls 20 together with the film retaining member 10 defining a U-shaped area 22 therebetween for accommodating the endodontic equipment, such as root canal files 24 and clamp 26 for the rubber dam 28. As can be seen from the drawings, the holder of the invention does not interfere with the endodontic files 24, the rubber dam 28, or its clamp 26.

As can be seen from FIGS. 2 and 4, the film retaining member 10 downwardly diverges from the side walls 20, in order to minimize bending of the X-ray film packet 18. The inner and outer tongues 12 and 14, are preferably centrally slottted or cut away, as shown in FIG. 5, to reduce bulk and facilitate unobstructed or shadowless X-ray access to the tooth. The film holder's legs thus defined by the two tongues are provided with nubs 15 thereon to provide additional gripping of the film packet 18.

The side walls 20 should be sufficiently high to accommodate the root canal files and to prevent the patient from driving the files 24 deeper into the tooth when biting down on the holder. In the preferred embodiment, the side walls 20 have windows 30 therein to provide maximum viewing of the subject tooth and root canal files 24.

In the preferred embodiment, the holder further comprises two top surface flanges 32, the transverse edges of each flange 32 being integral with the upper edge of the adjacent side walls 20, and the longitudinal edges of each flange 32 being integral with the upper edge of the adjacent portions of the member 10. The flanges 32 serve the purpose of rigidifying the holder and reinforcing the side walls 20 in relationship to the film retaining member 10. The top surface of the flanges 32 and bottom surface of the side walls 20 may be provided with gripping ridges 34 to insure that when positioned and held in place by the patient's bite, the holder will not slip before or during the radiograph procedure.

The holder further comprises a positioning arm 36. The positioning arm 36 is designated so that its long axis forms a 90° angle to the plane of the X-ray film packet. This is done so that the operator may utilize the positioning arm to guide the X-ray conehead into the appropriate position, according to whatever technique is being used. The long axis of the positioning arm also shows where the central ray of the X-ray should be directed. The arm 36 may be integral with either of the side walls 20 or may be removably attachable to either of the side walls 20. A suitable means for providing removable attachment of the positioning arm 36, is to provide the free end of each of the side walls 20 with the female portion of a conventional snap-in mechanism 38 and the end of the positioning arm 36 with the corrsponding male end of the snap-in mechanism. In this fashion, the position arm 36 may be removably attached to either of the side walls 20, as shown at 40. Other conventional removable attaching means may of course be used, provided there is no interference with the endodontic equipment.

The holder of the invention is preferably made from plastic by injection molding the same. Injection molded, clear polypropylene polymer has been found to be suitable. The film retaining member 10, side walls 20 and flanges 32 are preferably integral, although they may be separate pieces secured together by conventional means, depending upon the material. If a non-removable positioning arm 36 is desired, it may also be integral with one of the side walls 20.

The holder of the invention is used by a general dentist or an endodontist as follows: When a radiograph is desired, a X-ray film packet 18 is inserted into film retaining member 10 by pushing the packet 18 into the slot 16 between the inner tongue 12 and outer tongue 14. Thereby, the film packet 18 is held securely in place by the nubs 15. The dentist or endodontist then places the holder over the subject tooth, with the film packet 18 extending behind the tooth along the patient's inner gum line. The placement of the holder is readily accomplished by use of the positioning arm 36. As can be seen from FIG. 1, the side walls 20 of the holder are positioned over the two teeth adjacent the subject tooth, with the rubber dam clamp 26 and files 24 located within the U-shaped area 22 defined between the film retaining member 10 and the side walls 20. The dentist or endodontist can view the positioning of the files 24 from the open frontal area and from the sides through the windows 30 in the side walls 20. The dentist or endodontist may then adjust the position of the holder and film with the positioning arm 36. When the holder is in its desired position, the patient bites down on top of the holder, thereby securely holding the holder between his upper and lower teeth. The gripping ridges 34 assist in insuring that the holder does not slip from the desired position during the radiograph procedure. With the holder in place, the dentist or endodontist may then X-ray the subject tooth. In performing the radiograph procedure, the positioning arm 36 may be used as a guide in aiming the X-ray gun.

While the preferred embodiment of the invention has been shown and described herein, it is to be appreciated that various changes, rearrangements and modifications may be made therein without departing from the scope of the invention as defined by the appended claims.

What is claimed is:

1. A dental X-ray film holder especially useful in endodontics comprising: a film retaining member having an inner tongue and an outer tongue defining a slot therebetween for receiving a X-ray film packet; and two spaced apart side walls integral with the respective side edges of said film retaining member, said side walls being adapted to be held between the patient's upper and lower teeth and together with said film retaining member defining a U-shaped area therebetween for accommodating endodontic equipment.

2. A dental X-ray film holder as in claim 1, further comprising: two top surface flanges, the edges of each flange being integral with the upper edge of the adjacent side wall and the adjacent portions of the upper edge of said film retaining member.

3. A dental X-ray film holder as in claim 2, wherein the top surface of said flanges and the bottom surface of said side walls have a plurality of gripping ridges therein.

4. A dental X-ray film holder as in claim 1, further comprising a positioning arm attached to one of said side walls.

5. A dental X-ray film holder as in claim 1, further comprising a positioning arm; and means forremovably attaching said positioning arm to either of said side walls.

6. A dental X-ray holder especially useful in endodontics comprising: a film retaining member having an inner tongue and an outer tongue defining a slot therebetween for receiving a X-ray film packet; two spaced apart side walls integral with the respective side edges of said film retaining member, each of said side walls having windows therein, said side walls together with said film retaining member defining a U-shaped area therebetween for accommodating endodontic equipment; two top surface flanges each integral at their edges with the upper edges of the adjacent side wall and the upper edge of the adjacent portions of said film retaining member; the bottom surface of each of said side walls and the top surface of said flanges having gripping ridges therein adapted to engage the patient's upper and lower teeth; and a positioning arm removably attached to one of said side walls.

* * * * *